United States Patent [19]

Becker et al.

[11] 4,289,908

[45] Sep. 15, 1981

[54] PRODUCTION OF HIGHER AMINES BY THE GAS PHASE HYDROGENATION OF NITRILES

[75] Inventors: Eckhart R. Becker, Allentown; Randall J. Daughenbaugh, Barto; Barton Milligan, Coplay, all of Pa.

[73] Assignee: Air Products and Chemicals, Inc., Allentown, Pa.

[21] Appl. No.: 59,000

[22] Filed: Jul. 19, 1979

[51] Int. Cl.³ .............................................. C07C 85/12
[52] U.S. Cl. .................................... 564/490; 564/493; 564/497
[58] Field of Search ................. 260/583 K, 583 R, 690

[56] References Cited

U.S. PATENT DOCUMENTS

| | | | |
|---|---|---|---|
| 3,117,162 | 1/1964 | Rylander et al. | 260/583 K |
| 3,166,596 | 1/1965 | Miller et al. | 260/583 K |
| 3,177,258 | 4/1965 | Rylander et al. | 260/583 K X |
| 3,427,356 | 2/1969 | Baer et al. | 260/583 K |
| 3,468,953 | 9/1969 | Besson et al. | 260/583 K |
| 3,501,528 | 3/1970 | Rutzen | 260/583 K |
| 3,696,153 | 10/1972 | Kershaw et al. | 260/583 K |
| 3,972,938 | 8/1976 | Voges et al. | 260/583 K |

*Primary Examiner*—John Doll
*Attorney, Agent, or Firm*—E. Eugene Innis; Russell L. Brewer

[57] ABSTRACT

This invention relates to an improvement in a process for preparing lower acyclic saturated amines by the gas phase hydrogenation of nitriles. To carry out the gas phase hydrogenation, the temperatures utilized in the reaction zone are from about 150° to 350° C., the pressure from about atmospheric to 500 psia, and the space velocity from about 750–20,000. Preferably, the conditions are controlled such that the components in the reaction zone are not exposed to a temperature greater than 380° C. for a period of time in excess of 0.03 seconds.

5 Claims, No Drawings

4,289,908

PRODUCTION OF HIGHER AMINES BY THE GAS PHASE HYDROGENATION OF NITRILES

BACKGROUND OF THE INVENTION

1. Field

This invention relates to an improvement in a process for preparing acylic amines and the improvement resides in the vapor phase hydrogenation of the corresponding acyclic nitriles to form the amines.

2. Background of the Invention

U.S. Pat. No. 3,117,162 and U.S. Pat. No. 3,177,258 show hydrogenation reactions using a ruthenium-containing catalyst often combined with platinum, palladium or rhodium and the hydrogenation of nitriles (162) to form the corresponding amines. The 162 patent discloses that various nitriles, such as propionitrile and benzonitrile, can be hydrogenated at temperatures from 0°–400° C. in liquid phase and temperatures of 100°–400° C. with space velocities from 0.1–50 volumes vapor per volume of catalyst per hour under vapor phase conditions. The example shows that a high level of di-n-propylamine can be achieved by the liquid phase hydrogenation using rhodium on a carbon catalyst. Palladium on carbon resulted in a high concentration of the tertiary amine. As the temperature is increased, e.g. to 150° C., randomization of the amines product slate, particularly with rhodium, results.

German Patent No. 79,021 discloses a process for the continuous production of various ethylamines by hydrogenating acetonitrile over a fixed bed containing nickel or chromium catalyst. Hydrogenation is carried out at pressures from 5–230 atmospheres at temperatures between 100°–180° C. Selectivity to specific amines is achieved by operating a separation unit at temperatures from −33° to 50° C. and recycling the balance. Diethylamine in 91% yield was obtained at a separator temperature of 2° C. Acetonitrile was converted to monoethylamine in an 88% yield using a separator temperature of 29° C.

U.S. Pat. No. 3,468,953 discloses a process for preparing methylamines by the gas phase hydrogenation of hydrocyanic acid. The hydrogenation is carried out at a temperature from about 150°–300° C. in the presence of platinum metals preferably disposed upon diatomaceous earth or kaolin.

U.S. Pat. No. 3,427,356 discloses a process for preparing propylenediamines, particularly the primary amine, by hydrogenating aminopropionitriles. The hydrogenation is carried out in the presence of ammonia at temperatures below 200° C. using cobalt or nickel as the catalyst, the catalyst being promoted with a small amount of manganese.

U.S. Pat. No. 3,166,596 discloses a process for preparing a mixture of triethylenediamine and n-propylamine by reacting a mixture of acrylonitrile, hydrogen and aqueous ammonia under mild conditions in the presence of a hydrogenation catalyst. The reaction is carried out at a temperature from 50°–350° C. with pressures of from 15 to 200 atmospheres. Ratios of ammonia to acrylonitrile are approximately 5–40:1 on a molar basis with the balance being water. The product slate is sensitive to water, the higher the concentration of water the higher the concentration of n-propylamine.

U.S. Pat. No. 3,501,528 discloses the liquid phase hydrogenation of higher aliphatic or cycloaliphatic, nitriles having from 8 to 24 carbon atoms at temperatures of 220°–400° C. and pressures of from 50–400 atmospheres with excess hydrogen. Conventional hydrogenation catalysts, e.g. nickel, platinum, palladium, and the like are used.

Belgian Patent No. 860,470 discloses a liquid phase batch process for producing dipropylamine by the catalytic hydrogenation of acrylonitrile at a temperature of from 50°–130° C., and hydrogen pressure of from 1–60 bars. Long reaction times are utilized. A catalyst composed of rhodium on an inert support, e.g. alumina, silica and like is used. Yields of 65 to 83% dipropylamine at reaction temperatures from 75°–100° C. and pressures of 24 to 50 atmospheres are reported.

SUMMARY OF THE INVENTION

This invention relates to an improvement in a process for the synthesis of lower alkyl amines from acyclic mononitriles having from 2 to 8 carbon atoms in the structure. The improvement resides in the continuous gas phase synthesis of the amine by carrying out the reaction under conditions such that the acyclic mononitrile is reacted with hydrogen at a temperature and pressure such that the reactant and products are in the gas phase. The gas hourly space velocity is maintained from about 500–20,000. The temperature preferably is controlled to the extent that the maximum temperature in the hydrogenation zone does not exceed 380° C. for a period greater than 0.03 seconds.

There are several advantages associated with this gas phase process for producing acyclic amines. These advantages include:

an ability to produce amines and in particular propylamines in continuous manner;

an ability to control selectivity to amines, particularly dipropylamine by varying the gas hourly space velocity, temperature and feed composition, as opposed to the utilization of different catalysts alone or recycling substantial quantities of by-product amine, e.g. greater than a 1:1 mole ratio to the nitrile. Conventionally, such selectivity was available only through liquid phase reaction and prudent selection of catalyst;

an ability to use ammonia purge gas, synthesis gas, or other impure hydrogen source as a feedstock;

an ability to achieve high production rates suitable for commercial operation with excellent yield and selectivity of nitrile to amines;

an ability to manufacture amines with relatively simple reaction equipment and limited product purification equipment thus minimizing capital expenditures; and an ability to recover energy for commercial use by virtue of the high reaction temperature whereas such energy is not available from a low temperature liquid phase hydrogenation.

DESCRIPTION OF PREFERRED EMBODIMENTS

The gas phase generation of amines by the catalytic hydrogenation of nitriles has been difficult particularly with respect to acyclic mononitriles. The heat of reaction in the reduction of the nitrile to the amine is extremely high, e.g. 34 Kcal/mole and, therefore, the gas phase reduction has been avoided because attempts have been relatively unsuccessful. The higher temperatures associated with gas phase reduction resulted in cracking of the aliphatic or acyclic mononitriles producing hydrocarbons. In other words, yield and selectivity of amines produced in accordance with previous gas phase processes (without recycling substantial amine by-product) has been poor.

The present invention is applicable to the gas phase reduction of acyclic mononitriles having from 2 to 8 carbon atoms in the structure. These nitriles include propionitrile, butyronitrile, isobutyronitrile, acetonitrile and acrylonitrile. Acrylonitrile and other unsaturated nitriles of appropriate carbon content are considered to be acceptable feedstocks in view of the fact that these nitriles are first hydrogenated at the unsaturated site and then subsequently reduced to the amine. Thus, one could use acrylonitrile or other unsaturated nitrile as the mononitrile since the conditions for conversion of the nitrile (subsequent to the hydrogenation of the unsaturated site) would remain the same.

To understand gas phase reduction of nitriles by this invention, certain reaction mechanisms are reviewed. It is wellknown that the extent of reaction is determined by the minimum free energy of the system. This thermodynamic equilibrium in product composition is determined by the temperature, pressure, and initial composition of the reactant mixture. This invention utilizes the features of thermodynamic equilibrium to manufacture, with adjustable selectivity, the proportion of mono, di and triamines, particularly from proprionitrile. For example, the selectivity of the nitrile hydrogenation is adjusted by controlling the extent of reaction through suitable temperature, pressure and inlet composition and the extent of reaction as determined by contact time. Although not intending to be bound by theory, these mechanisms which follow help to explain the reaction chemistry developed herein in amine formation. The arrows and lengths are indicative of the direction of the reaction and the rate at which the reaction proceeds. A long arrow then suggests a fast rate.

transfer limited. Based on our observation we have found that the gas phase operation should be conducted under temperatures sufficiently high for effecting hydrogenation of the nitrile but at a bulk temperature below about 380° C. maximum T(MAX) and preferably below 350° C. Concomitant with this temperature control is the requirement that the reactants and product are not exposed to this maximum temperature for a period of greater than 0.03 seconds and preferably not longer than 0.01 seconds. This latter feature often is expressed in terms of gas hourly space velocity (GHSV). The GHSV generally is proportional with the reaction temperature and thus slightly lower temperatures will permit a slightly lower GHSV without adversely affecting the product slate. However, once the conditions exceed the values within the range specified then adverse results begin to appear particularly in terms of increased hydrocarbon formation and decreased yield.

In carrying out the gas phase process there are several factors, as can be seen from the Amine-Hydrogen chemistry network, which enter into effecting reduction of the nitrile with high yield, good selectivity, and an ability to obtain a desirable product slate with minimal recycling of various amines. These general conditions are as follows:

First, the reactor used for the gas phase hydrogenation should be manufactured from a material which permits rapid heat removal from the unit. The material must also be resistant to corrosion by the reactants and product slate as well as byproducts which can be produced in the unit. Stainless steel, tantalum, Hastelloy steel, carbon steel and others are suited materials. The reactor may be a fluidized bed reactor or fixed bed reactor. Preferably, the reactor is tubular in shape and of a small diameter so that there is a substantial surface

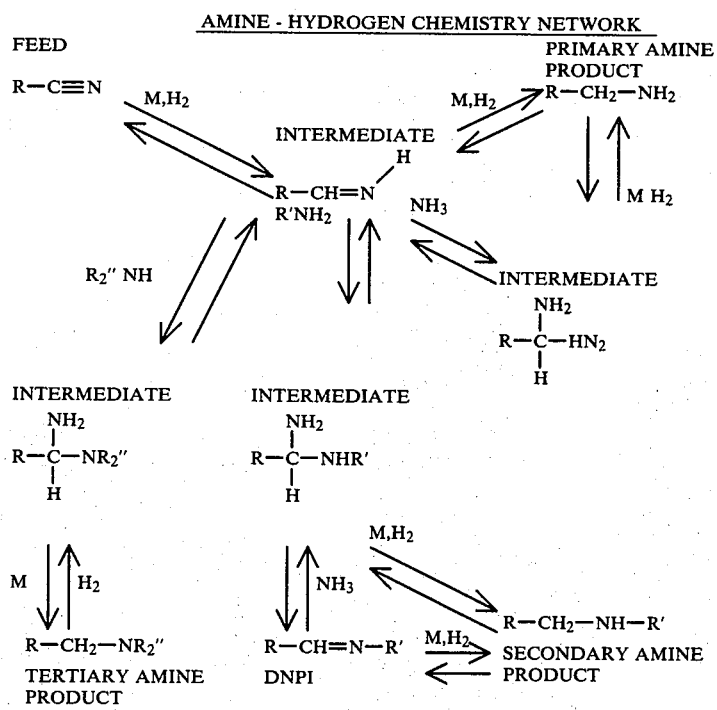

The gas phase technique for reducing nitriles to the amine generally is heat transfer limited and is distinguished from liquid phase reduction which is mass area; this will permit good heat transfer. As a guide, for a fixed bed reactor, a ratio of the length (L) (catalyst length) to the diameter (L/D) of the reactor is from about 5 to 500, and preferably from 150-250. As would be expected, the smaller the ratio (L/D) the greater the need for increased cooling capacity. Suggested dimensions for the reactor are from about 0.5 to 3 inches in diameter to lengths of about 10 to 30 feet. For a fluidized bed reactor, the ratio may be much higher.

The feed composition is important in defining the product slate. By this invention, it is possible to avoid the use of by-products as diluent in order to maintain process control. The use of by-product amine as recycle of course reduces the output of the reactor and requires greater load on the separation equipment. Feed ratios should be 0-4 moles of amine to nitrile, and preferably 0-1 moles amine per mole nitrile. Any higher concentrations adversely affect the plant output.

The ratio of hydrogen to nitrile on a molar basis is extremely important. As the ratio decreases to stoichiometric, the greater the heat load on the system for a given space velocity and the more difficult it is to maintain temperatures and therefore maintain a desirable product slate. This stoichiometric ratio also favors coke formation which has a deleterious effect on catalyst life. We have found that as the ratio of hydrogen to nitrile approaches about 2 moles hydrogen per mole nitrile the more difficult it is to control the process. It is preferred that hydrogen molar ratios from 2.5 to 6 per mole of nitrile are used. Higher ratios give good results in terms of product but such ratios result in excess power consumption due to the need for hydrogen recycle.

To control temperatures, maintain an appropriate GHSV, and/or maintain the reaction above the dew point temperature, it is often necessary to add a diluent gas such as ammonia, nitrogen or excess hydrogen. Quantities of ammonia or nitrogen based upon the nitrile content can be adjusted from 0 to 50, generally 0.1-10 moles per mole of nitrile depending on process economics and feed hydrogen composition. Ammonia can be recycled to the reactor as desired in a case where one wants to produce high yields of the monoamine. Note, from the Amine-Hydrogen chemistry network, the formation of the monoamine by the addition of ammonia to the first intermediate. As a side benefit, one of the advantages of the process is that because the system can effectively utilize a diluent gas, the hydrogen source may be ammonia purge gas or ammonia synthesis gas, i.e. one containing methane, nitrogen, etc.

The gas hourly space velocity GHSV, which is the gas volume throughput at standard temperature and pressure per volume catalyst, is extremely important in order to maintain the appropriate temperatures in the reaction zone. It also influences the product slate that is formed. Generally, the gas hourly space velocity is from 500-20,000, and preferably 2,000-12,000. This gives a residence time in the reaction zone of from about 0.1 to about 2.5 seconds. A GHSV any lower than 500 makes it difficult for commercial operation.

Due to the exothermicity of the reaction, the temperature in a reactor under given feed flow rates may not be uniform throughout the reactor. The magnitude of the deviation from the inlet temperature and T(MAX) depends upon the efficiency of the heat removal of the reactor. When an inlet temperature is higher than about 200° C., e.g. 250° with the tubular reactors previously described, it may be difficult to maintain appropriate reaction conditions within the T(MAX), particularly at a high GHSV.

Hydrogenation conditions, e.g. hydrogen pressure and catalysts used are essentially the same as those used heretofore. Pressures can be from atmospheric to about 2000 psig. Preferred ranges are 150-400 psig. Generally, the pressures are selected to accomodate product recovery and not the reaction. Higher pressures of course require more expensive equipment.

Metals suited for catalyzing the reduction of the nitrile include those commonly used for hydrogenation reactions such as cobalt, nickel, rhodium, ruthenium, platinum, palladium, etc. These metals optionally can be carried upon a catalytic support such as silica, alumina, kieselguhr, kaolin, charcoal, and so forth. For preferred results Raney nickel, nickel on alumina or rhodium or palladium on gamma alumina are used.

The following examples are provided to illustrate preferred embodiments of the invention of and are not intended to restrict the scope thereof. All parts are parts by weights unless otherwise specified and all percentages are weight percent.

EXAMPLE 1

A glass tube reactor was designed which consisted of a 1 inch outside diameter Pyrex tube having a thermocouple well inserted in the center. The tube had a length of approximately 26 inches, the first section consisting of a 13 inch preheater section and the second consisting of a 13 inch catalyst bed section. The glass tube reactor then was connected to a water cooled condenser so that product coming from the reactor would be condensed. The glass tube reactor was filled 100 cc of with a finely divided catalyst initially containing 42% nickel oxide carried on a gamma alumina support. The nickel oxide was reduced at 750° F. with hydrogen. The surface area was approximately 190 m²/g. The catalyst was supplied under the trademark HSC-102 by the Houdry Division of Air Products and Chemicals, Inc.

Several runs were made as reported in Table 1 below, which show variation in feedstock, rate in ml/minute as measured at ambient temperatures e.g. propionitrile (PRN) and acrylonitrile (ACRN) and with varying rates of nitrogen as diluent to keep the reaction in the gas phase and hydrogen at STP. The product as it was obtained from the boiler condenser was sampled and analyzed by gas chromatography for mononormalpropylamine (MNPA), propionitrile (PRN), dinormalpropylimine (DNPI), dinormalpropylamine (DNPA) and trinormalpropylamine (TNPA).

TABLE 1

| Experiment | Feedstock | Inlet Temp. °F. | °C. | Feed Rate ml/min. | $N_2$ Ft.$^3$/Hr. | $H_2$ Ft.$^3$/Hr. | GHSV | Product GC Area Percents | | | | | |
|---|---|---|---|---|---|---|---|---|---|---|---|---|---|
| | | | | | | | | MNPA | PRN | DNPI | DNPA | TNPA | Misc. |
| 1 | PRN | 400 | 204 | 0.89 | 3.25 | 3.4 | 2000 | 18.4 | 14.8 | 1.8 | 50.3 | 11.5 | 1.6 |
| 2 | PRN | 400 | 204 | 0.75 | 1.5 | 3.4 | 1500 | 30.2 | 4.7 | 1.1 | 57.6 | 5.2 | 1.2 |
| 3 | PRN | 200 | 93 | 0.37 | 1 | 3.4 | 1300 | 2.2 | 89.6 | 4.4 | 1.7 | 0.6 | — |
| 4 | PRN | 500 | 260 | 0.75 | 1.5 | 3.4 | 1500 | 2.5 | 2.1 | 1.3 | 55.6 | 29.2 | 4.9 |
| 5 | PRN | 500 | 260 | 0.75 | 1.5 | 3.4 | 1500 | 15.7 | 4.5 | 1.1 | 55.2 | 16.1 | 3.1 |
| 6 | PRN | 610 | 321 | 0.63 | 2 | 3.4 | 1650 | 6.0 | 80.8 | 0.9 | 2.6 | 1.6 | 0.5 |
| 7 | ACRN | 530 | 276 | 0.88 | 4 | 3.4 | 2300 | 3.9 | 65.7 | 1.7 | 17.0 | 4.9 | 5.55 |

TABLE 1-continued

| Experiment | Feedstock | Inlet Temp. °F. | °C. | Feed Rate ml/min. | N₂ Ft.³/Hr. | H₂ Ft.³/Hr. | GHSV | MNPA | PRN | DNPI | DNPA | TNPA | Misc. |
|---|---|---|---|---|---|---|---|---|---|---|---|---|---|
| 8 | ACRN | 530 | 276 | 0.88 | 4 | 3.4 | 2300 | 13.1 | 19.9 | 2.7 | 46.5 | 15.9 | 1.1 |
| 9 | ACRN | 350 | 176 | 0.39 | 2.5 | 3.4 | 1750 | 3.4 | 54.1 | 5.7 | 11.1 | 2.5 | 3.8 |

Although it was difficult to maintain a good mass balance for the above runs, (Table 1) product conversions to di n-propylamine averaged from about 25–50%. Temperature control was extremely difficult in the glass tube and the glass tube melted during one operation. The results merely show that gas phase hydrogenation can be carried but that more precise control to reduce the proportion of the hydrocarbons in the reaction product as noted in the miscellaneous column and a better understanding of operating conditions would be necessary to determine if gas phase hydrogenation has commercial merit.

EXAMPLE 2

Several runs of different feedstocks were made in a process design unit reactor which consisted of half inch (0.41 inches I.D.) 304 stainless steel tubing encased in an aluminum block. The reactor was Model R-100 designed by the Ace Catalyst Company. This reactor had a preheater zone and a reactor zone with a reactor temperature being limited to 650° F., and pressure limited to 900 psi at 600° C. The reactor utilized electrical heat for temperature control. In runs 1–13 the catalyst used was palladium on gamma alumina, the palladium being present in 0.5% by weight. The surface area was approximately 80 m²/g and the pore volume of 0.46 cc/gm. The reactor was charged with 10 cc catalyst to provide a reactor zone bed depth of about 10 centimeters. In runs 13–21 the catalyst was rhodium on gamma alumina, the rhodium concentration being 1% by weight. The surface area was 225 m²/g and the pore volume 0.84 cc/gm. The results are shown in Table 2. The product weight ratio is reported on a basis of 1 weight part di-n-propylamine.

TABLE 2

| Run | Inlet Temp. °C. | psia | GHSV | Feed Composition Wt % | | | | % Conversion | % Yield[b] | Product Weight Ratio | | |
|---|---|---|---|---|---|---|---|---|---|---|---|---|
| | | | | H₂ | N₂ | Nitrile | MNPA | | | MNPA | DNPA | TNPA |
| 1 | 100 | 55 | 534 | 12.5 | — | PRN 87.5 | — | 41 | 98 | 0 | 0 | 1 |
| 2 | 100 | 165 | 2250 | 2.3 | 81.4 | PRN 16.2 | — | 28 | 99 | 0 | 0 | 1 |
| 3 | 200 | 55 | 788 | 13.2 | — | PRN 86.8 | — | 50 | 98 | 0 | 1 | 1.96 |
| 4 | 200 | 55 | 2240 | 13.1 | — | PRN 86.8 | — | 8 | 99 | 0 | 1 | 1.47 |
| 5 | 350 | 165 | 2390 | 2.4 | 82.3 | PRN 15.4 | — | 22.6 | 90.5 | 0 | 1 | 0.16 |
| 6 | 350 | 198 | 742 | 22.1 | — | PRN 77.9 | — | 85 | 89.6 | 0.60 | 1 | 0.12 |
| 7 | 350 | 305 | 1500 | 18.8 | — | PRN 64.0 | 17.1 | 40.6 | 95.3 | 0.44 | 1 | 0.32 |
| 8 | 350 | 66 | 751 | 6.9 | — | PRN 93.1 | — | 20 | 91.4 | 0.50 | 1 | 0.14 |
| 9 | 350 | 132 | 785 | 7.2 | — | PRN 92.8 | — | 50.1 | 87.8 | 0.55 | 1 | 0.21 |
| 10 | 350 | 107 | 1510 | 5.4 | — | PRN 74.7 | 20.0 | 32 | 75.7 | 2.43 | 1 | 0.09 |
| 11 | 180 | 180 | 1500 | 7.0 | — | ACRN 93.0 | — | 100 | 100[c] | — | — | — |
| 12 | 120 | 180 | 1500 | 7.0 | — | ACRN 93.0 | — | 100 | 100[d] | — | — | — |
| 13 | 80 | 180 | 1500 | 7.0 | — | ACRN 93.0 | — | 99.5 | 100[e] | — | — | — |
| 14 | 80 | 180 | 2999 | 7.0 | — | ACRN 92.9 | — | 60 | 100[e] | — | — | — |
| 15 | 200 | 173 | 1500 | 10.4 | — | PRN 70.7 | 18.9 | 100 | 98.8 | 0.26 | 1 | 0.69 |
| 16 | 250 | 173 | 1500 | 10.4 | — | PRN 70.7 | 18.9 | 100 | 96.6 | 0.41 | 1 | 0.32 |
| 17 | 250 | 305 | 1500 | 18.9 | — | PRN 64.0 | 17.1 | 100 | 96.9 | 0.34 | 1 | 0.42 |
| 18 | 350 | 173 | 1500 | 10.4 | — | PRN 70.7 | 18.9 | 73 | 86.7 | 5.35 | 1 | 8.27 |
| 19 | 300 | 305 | 1500 | 18.9 | — | PRN 64.0 | 17.1 | 100 | 93.4 | 0.53 | 1 | 0.21 |
| 20 | 300 | 173 | 3010 | 10.4 | — | PRN 70.7 | 18.9 | 99 | 96.5 | 0.48 | 1 | 0.25 |
| 21 | 200 | 173 | 1500 | 10.4 | — | PRN 70.7 | 18.9 | 66 | 97.8 | 0.06 | 1 | 0.54 |
| 22 | 100 | 180 | 1421 | 6.5 | — | ACRN 93.5 | — | 100 | 99.3[f] | — | — | — |

These runs in general show that selectivity is relatively independent of catalyst. As the temperature is increased the greater the concentration of mono and di-n-propylamine. The reaction is not as influenced by pressure, but it has some effect (compare runs 7–9). Most of the effect is related to space velocity at a given conversion. On review of the Amine-Hydrogen Network, the formation of tri-n-propylamine requires that the reaction be allowed to proceed toward equilibrium, the primary and secondary amine being formed initially. Runs 1 and 3 show this feature using low space velocity to form tri-n-propylamine. Runs 7–10 and 14–16, 18 and 20 show high selectivity to di-n-propylamine with palladium or rhodium catalysts at feedstock inlet temperatures of from 200–350° C. and a space velocity of 750—3,000.
[a]Runs 1–14 utilized 0.5% palladium or gamma alumina as catalyst. Runs 14–21 utilized 1.0% rhodium on gamma alumina.
[b]Yield is defined as 100% minus all non-recyclable compounds.
[c]includes 97.51% PRN, 0.23% DNPA and 1.61% TNPA
[d]includes 99.87% MNPA and 0.09% TNPA
[e]PRN sole product
[f]includes 96.5% PRN, 0.07% MNPA, 0.55% PNPA and 0.39% TNPA

EXAMPLE 3

The procedure of Example 2 was repeated except with the modification that a thermocouple well was inserted into the center of the reactor and the temperature measured over the entire length of the reactor during the run. The catalyst used in Runs 1–8 and 11–30 was an 8% Ni/Al₂O₃ catalyst. Runs 9 and 10 used a 20% cobalt on alumina catalyst. Runs 31–34 were performed with a commercial cobalt on alumina catalyst which was coded G62 by United Catalyst Co. The catalysts were added in an amount to provide a 5 cc bed depth or a bed depth of ½ that in Example 2. The process parameters were varied and results obtained as noted in Table 3.

The gas flow rate for this series of runs is in ml/minute and the nitrile amine feed rate in ml/hour. A feed rate of 382 ml/min H₂ 475 ml/min N₂ and 12 ml/hr PRN provides the following mole proportion 4 H₂, 4 N₂ and 1 PRN.

TABLE 3

| Run | Inlet Temp. °C. | T Max | Time T Max Seconds | psia | GSHV | Feed Composition ml/min H₂ | N₂ | PRN | ml/hr MNPA | TNPA | % Conversion | Yield | Selectivity Ratio MNPA | DNPA & DNPI | TNPA |
|---|---|---|---|---|---|---|---|---|---|---|---|---|---|---|---|
| 1 | 138 | N.R. | N.R. | 171 | 11,000 | 382 | 475 | 12 | — | — | 34.3 | 100 | 0.58 | 1 | 0.0004 |
| 2 | 138 | N.R. | N.R. | 171 | 11,000 | 382 | 475 | 12 | — | — | 18 | 100 | 0.68 | 1 | 0.01 |
| 3 | 138 | N.R. | N.R. | 250 | 11,000 | 382 | 475 | 12 | — | — | 24.7 | 100 | 0.83 | 1 | 0 |
| 4 | 138 | N.R. | N.R. | 251 | 5,500 | 191 | 238 | 6 | — | — | 38.4 | 100 | 1.22 | 1 | 0.001 |
| 5 | 139 | N.R. | N.R. | 250 | 2,210 | 76.4 | 95 | 2.4 | — | — | 71.8 | 100 | 2.2 | 1 | 0 |
| 6 | 143 | N.R. | N.R. | 250 | 11,000 | 382 | 475 | 12 | — | — | 99.8 | 100 | 1.0 | 1 | 0.1 |
| 7 | 143 | N.R. | N.R. | 250 | 11,000 | 382 | 475 | 12 | — | — | 100 | 99.3 | 0.86 | 1 | 0.13 |
| 8 | 143 | N.R. | N.R. | 49 | 11,000 | 382 | 475 | 12 | — | — | 99.9 | 100 | 0.84 | 1 | 0.1 |
| 9 | 140 | N.R. | N.R. | 121 | 11,400 | 382 | 475 | 18 | — | — | 99.8 | 96.8 | 2.4 | 1 | 0.01 |
| 10 | 140 | N.R. | N.R. | 122 | 11,400 | 382 | 475 | 18 | — | — | 79 | 99 | 0.5 | 1 | 0.002 |
| 11 | 145 | N.R. | N.R. | 248 | 11,400 | 407 | 407 | 19 | — | — | 26 | 100 | 1.1 | 1 | 0 |
| 12 | 158 | N.R. | N.R. | 248 | 11,000 | 407 | 407 | 19 | — | — | 90 | 97.0 | 0.877 | 1 | 0.074 |
| 13 | 158 | N.R. | N.R. | 251 | 11,000 | 407 | 407 | 19 | — | — | 91.1 | 95.3 | 0.961 | 1 | 0.071 |
| 14 | 153 | N.R. | N.R. | 248 | 10,000 | 407 | 407 | 9.5 | — | — | 90 | 98.1 | 1.1 | 1 | 0.003 |
| 15 | 138 | N.R. | N.R. | 253 | 10,000 | 81.5 | 81.5 | 4.0 | 4.0 | 1.0 | 75 | 93.6 | 2.45 | 1 | 0.307 |
| 16 | 148 | N.R. | N.R. | 255 | 10,000 | 81.5 | 81.5 | 4.0 | 4.0 | 1.0 | 83 | 95.6 | 2.8 | 1 | 0.40 |
| 17 | 157 | N.R. | N.R. | 253 | 10,000 | 81.5 | 81.5 | 4.0 | 4.0 | 1.0 | 98 | 97.7 | 3.4 | 1 | 0.31 |
| 18 | 135 | 146 | 0.65 | 251 | 11,000 | 407 | 407 | 19.0 | — | — | 19.4 | 99.6 | 1.24 | 1 | 0.02 |
| 19 | 135 | 145 | 0.16 | 251 | 5,500 | 204 | 204 | 9.5 | — | — | 32.5 | 100 | 1.6 | 1 | 0.01 |
| 20 | 141 | 153 | — | 248 | 2,200 | 81.4 | 81.4 | 3.8 | — | — | 84.2 | 100 | 2.8 | 1 | 0.005 |
| 21 | 141 | 152 | 0.16 | 249 | 5,500 | 204 | 204 | 9.5 | — | — | 35.5 | 100 | 1.45 | 1 | 0.006 |
| 22 | 141 | 152 | 0.03 | 250 | 11,000 | 407 | 407 | 19 | — | — | 17.9 | 100 | 1.1 | 1 | 0.1 |
| 23 | 146 | 158 | 0.65 | 249 | 2,200 | 81.4 | 81.4 | 3.8 | — | — | 76.5 | 100 | 2.6 | 1 | 0.006 |
| 24 | 146 | 162 | 0.13 | 250 | 5,500 | 204 | 204 | 9.5 | — | — | 42 | 98.0 | 1.4 | 1 | 0.007 |
| 25 | 151 | 169 | 0.13 | 250 | 5,500 | 204 | 204 | 9.5 | — | — | 45.1 | 100 | .25 | 1 | 0.006 |
| 26 | 156 | 180 | 0.13 | 250 | 5,500 | 204 | 204 | 9.5 | — | — | 52.4 | 100 | 1.3 | 1 | 0.005 |
| 27 | 161 | 254 | 0.06 | 249 | 5,500 | 204 | 204 | 9.5 | — | — | 96.9 | 97.2 | 1.1 | 1 | 0.6 |
| 28 | 136 | 250 | 0.03 | 253 | 11,000 | 407 | 407 | 19.0 | — | — | 99.8 | 98.8 | 0.84 | 1 | 0.14 |
| 29 | 170 | 232 | — | 250 | 5,500 | 204 | 204 | 9.5 | — | — | 68.4 | 100 | 0.54 | 1 | 0.13 |
| 30 | 195 | 227 | — | 250 | 5,500 | 204 | 204 | 9.5 | — | — | 33.3 | 100 | 0.39 | 1 | 0.11 |
| 31 | 140 | 175 | — | 250 | 2,200 | 81.5 | 81.5 | 31.8 | — | — | 100 | 98 | 0.64 | 1 | 0.09 |
| 32 | 120 | 158 | — | 250 | 2,200 | 81.5 | 81.5 | 3.8 | — | — | 100 | 98 | 1.6 | 1 | 0.05 |
| 33 | 125 | 170 | — | 250 | 2,200 | 81.5 | 81.5 | 3.8 | — | — | 100 | 95 | 2.1 | 1 | 0.02 |
| 34 | 125 | 187 | — | 250 | 5,500 | 204 | 204 | 9.5 | — | — | 98 | 87 | 2.2 | 1 | 0.06 |

N.R. = Not Recorded
PRN = Propionitrile
MNPA = n-propylamine
DNPI = di-n-propylimine
DNPA = di-n-propylamine
TNPA = Tri-n-propylamine In reviewing Table 3, the high concentrations of MNPA are shown in Runs 5, 9, 20, 33 and 34. With nickel catalysts, low conversions result in high MNPA while high conversions are required with the cobalt catalyst. Based on the Amine-Hydrogen Network then, it can be seen that the rate for moving toward equilibrium is faster with nickel than with cobalt.

DNPA is formed with good selectivity in Runs 1, 2, 10 and 31. Slightly higher temperatures were generated during the reaction thereby permitting the reaction to proceed toward equilibrium. The higher temperatures resulted because of the higher heat generation due to the increased space velocity as compared to those in Runs 5, 9, etc. where MNPA was produced. To summarize Runs 1, 2, 10 and 31, reaction temperatures of from 140°-180° C. with a space velocity of 6,000-12,000 result in high DNPA production.

EXAMPLE 4

An isothermal study of the gas phase hydrogenation of propionitrile to propylamine was continued through evaluation of a recycle reactor manufactured by Autoclave engineers. The model was a Berty recycle reactor. The Berty reactor was tubular in shape having a one inch diameter and was filled with 25 cc of ⅛th inch extrudate catalyst, the catalyst containing 8% nickel and supported on alumina. The feed composition comprised 4 moles hydrogen to 1 mole of propionitrile with the ratio of hydrogen to nitrogen being a 3:1 mole ratio. The gas hourly space velocity was maintained at 1750 hrs.$^{-1}$.

Table 4 presents the results obtained by this isothermal hydrogenation. RPM represents the rotation speed of the agitator, the higher the speed, the less the temperature differential. T°C. represents the average temperature in degrees centigrade. M, D and T represent the weight selectivity ratio of mono, di and tripropylamine.

TABLE 4

AUTOCALVE ENGINEERS BERTY RECYCLE REACTOR DATA

| RUN | T° C. | CONV. % | RPM | YIELD % | M | D | T |
|---|---|---|---|---|---|---|---|
| 1 | 157 | 95 | 500 | 98 | 1.4 | 1 | 0.4 |
| 2 | 157 | 95 | 500 | 98.5 | 1.4 | 1 | 0.4 |
| 3 | 152 | 94 | 500 | 97 | 1.3 | 1 | 0.5 |
| 4 | 142 | 93 | 500 | 99.5 | 1.2 | 1 | 0.4 |
| 5 | 142 | 93 | 1000 | 99.6 | 1.2 | 1 | 0.5 |
| 6 | 142 | 93 | 1000 | 99.5 | 1.2 | 1 | 0.5 |
| 7 | 142 | 93 | 1000 | 99.5 | 1.2 | 1 | 0.5 |
| 8 | 129 | 62 | 500 | 99 | 2.2 | 1 | 0.02 |
| 9 | 127 | 71 | 500 | 99 | 2.2 | 1 | 0.02 |
| 10 | 125 | 74 | 500 | 99 | 2.0 | 1 | 0.03 |
| 11 | 132 | 90 | 1500 | 99 | 1.5 | 1 | 0.1 |
| 12 | 132 | 90 | 1500 | 99 | 1.5 | 1 | 0.1 |
| 13 | 132 | 90.5 | 1500 | 99 | 1.4 | 1 | 0.2 |
| 14 | 132 | 90.5 | 1500 | 99 | 1.4 | 1 | 0.2 |
| 15 | 109 | 38.5 | 500 | 99.5 | 1.8 | 1 | 0.02 |
| 16 | 110 | 43 | 500 | 99 | 1.5 | 1 | 0.03 |
| 17 | 110 | 49 | 500 | 99 | 1.5 | 1 | 0.04 |
| 18 | 111 | 49 | 500 | 99 | 1.4 | 1 | 0.05 |
| 19 | 113 | 63 | 1000 | 99 | 1.4 | 1 | 0.08 |

TABLE 4-continued
AUTOCALVE ENGINEERS BERTY RECYCLE REACTOR DATA

| RUN | T° C. | CONV. % | RPM | YIELD % | M | D | T |
|---|---|---|---|---|---|---|---|
| 20 | 114 | 67 | 1000 | 99 | 1.3 | 1 | — |
| 21 | 114 | 70 | 1500 | 99 | 1.5 | 1 | — |
| 22 | 169 | 94 | 500 | 99 | 1.1 | 1 | 0.3 |
| 23 | 169 | 95 | 1000 | 99 | 1.1 | 1 | 0.4 |
| 24 | 169 | 95 | 1000 | 99 | 1.1 | 1 | 0.4 |
| 25 | 169 | 95 | 1000 | 99 | 1.1 | 1 | 0.4 |

The results in Table 4 show that temperatures above about 140° C. are required to obtain a conversion above about 90% at a relatively low space velocity (by this isothermal process) of 1750 hrs.$^{-1}$. The results also show that at high conversion, e.g. above 95% at moderate isothermal temperatures, e.g. 150° (that a high proportion of the triisomer is formed, e.g. 0.4 to 0.6 moles per mole of diisomer). As the temperature is reduced and conversion falls, there generally is a lesser amount of the triisomer with the corresponding increase in the level of the monoisomer. For example, Runs 8-10, which operate at temperatures of about 125° C., result in a conversion of 75%, have a high ratio of mono to di to tri, e.g. 2.2./1/0.02. As the temperature increases from 130 to 140° C. range, at the same space velocity, the concentration of the triisomer increases with a corresponding decrease in the monoisomer.

To summarize the data in Table 4, and correlate it to the amine-hydrogen chemistry network, it is clear that if one wants to control the proportion of isomers in the reaction product, this can be done by an appropriate selection of reaction temperatures, to give desired conversion and then correlate contact time. Thus, when high inlet reaction temperatures are used, e.g. 140°-160° C., which results in high conversion, e.g. greater than 95%, the space velocity must be reduced toward the lower end of the scale, e.g. from 500-2000 hrs.$^{-1}$ in order to have a high triisomer content. This is consistent with the Amine-Hydrogen chemistry network analysis which suggests that as the reaction proceeds toward equilibrium, a higher concentration of tertiary amine will be produced. The results also show that as conversion is reduced by the use of low reaction temperatures, e.g. 100°-125° C., then high proportions of the mono and diisomer are obtained. Alternatively, high proportions of mono and diisomer can be achieved by operating at high temperatures, e.g. 180°-300° C. and controlling the contact time so that the reaction does not proceed to equilibrium, e.g. utilizing a space velocity of 9,000-14,000 hrs.$^{-1}$.

What is claimed is:

1. In a process for the catalytic hydrogenation of a lower aliphatic mononitrile having from 2 to 6 carbon atoms in a structure by reacting said nitrile with hydrogen in a reaction zone to form the corresponding amine, the improvement which comprises:
    (a) carrying out said reaction at a temperature and pressure such that the hydrogenation reaction is carried out in the gas phase; and
    (b) maintaining a feed throughput in the reaction zone such that the gas hourly space velocity is from 2,000 to 12,000.

2. The process of claim 1 wherein said mononitrile is propionitrile.

3. The process of claim 2 wherein from about 0-4 moles monopropylamine are recycled and combined per mole of feed propionitrile in the reaction zone.

4. The process of claim 1 wherein the molar ratio of hydrogen to lower acyclic mononitrile is from 2.5 to 6.

5. The process of claim 4 wherein the catalyst employed in the hydrogenation is selected from the group consisting of cobalt, nickel, platinum, palladium and rhodium.

* * * * *